United States Patent [19]

Shirakura et al.

[11] Patent Number: 4,676,379
[45] Date of Patent: Jun. 30, 1987

[54] APPARATUS FOR SORTING OUT DEFECTIVE PLASTIC CRATES FOR BOTTLES

[75] Inventors: Akira Shirakura; Ichiro Yonezawa; Shuichi Yokokura, all of Takasaki, Japan

[73] Assignee: Kirin Beer Kabushiki Kaisha, Tokyo, Japan

[21] Appl. No.: 717,602

[22] Filed: Apr. 1, 1985

Related U.S. Application Data

[63] Continuation of Ser. No. 454,665, Dec. 30, 1982, abandoned.

[30] Foreign Application Priority Data

Jan. 9, 1982 [JP] Japan .................................. 57-2009

[51] Int. Cl.⁴ .............................................. B07C 5/34
[52] U.S. Cl. .................................... 209/599; 209/559; 209/600; 73/573
[58] Field of Search ............... 209/559, 560, 571, 599, 209/600, 921, 572; 73/1 DV, 11, 12, 573, 82, 634, 575

[56] References Cited

U.S. PATENT DOCUMENTS

| | | | |
|---|---|---|---|
| 2,277,037 | 3/1942 | Clark et al. | 209/599 X |
| 3,003,628 | 10/1961 | Diamond et al. | 209/599 |
| 3,302,454 | 2/1967 | Kleesattel | 73/67.1 |
| 3,688,567 | 9/1972 | Thorwest et al. | 209/599 |
| 3,693,400 | 9/1972 | Savit | 73/1 DV |

Primary Examiner—Robert B. Reeves
Assistant Examiner—Glenn B. Foster
Attorney, Agent, or Firm—Ladas & Parry

[57] ABSTRACT

An apparatus for discriminating and sorting out defective plastic bottle crates from sound bottle crates comprising driving means for urging an indenter or contact tip provided at the tip of a vibrating rod of an ultrasonic hardness tester into steady contact in indented state with a bottle crate, detecting means for detecting resonant frequency of said vibrating rod which is varied by the urging of said indenter or contact tip into steady contact with said bottle crate, and means for distinguishing and sorting out defective bottle crates from sound bottle crates in response to the resonant frequency detected by the detecting means.

5 Claims, 7 Drawing Figures

APPARATUS FOR SORTING OUT DEFECTIVE PLASTIC CRATES FOR BOTTLES

This is a continuation of co-pending application Ser. No. 454,665 filed on Dec. 30, 1982, now abandoned.

BACKGROUND OF THE INVENTION

This invention relates to an apparatus for sorting out defective plastic crates for containing a plurality of articles such as beer bottles for transportion thereof.

Plastic materials from which such plastic crates (hereinafter referred to most often as "crates") are produced are generally polyethylene, polypropylene and copolymers thereof. However, when these plastics are used for a long period of time, the molecular weight at the surface thereof tends to be reduced particularly by sunlight rays to cause fine cracks, and these plastics tend to become brittle.

Accordingly, when crates made of such plastic materials are used for a long period of time, the strength thereof is gradually lowered and eventually the crates become unusable. More specifically, crates having lowered strength are subject to damage or breakage due to handling and/or stacking during distribution. Further, when a crate breaks on a production line of a bottling factory, the production may be obstructed.

However, no inspection of such crates has been carried out in the past. This is because plastic bottle crates began to be first used around 1965, and only about 16 years have elapsed even for initially produced crates. Therefore, even if the quality of these crates has deteriorated to some extent, their deterioration has not heretofore been of an extent such as to preclude their use.

However, there is a possibility that decrease in strength with long period of use will cause an increase in crates which cannot withstand use. Thus, while there may be a process wherein the crates are inspected or sorted out on the basis of their production years, such a process is not suitable because the strength decrease of the crates varies depending upon the state of use of the individual crates.

While there may be another process wherein the degree of the deterioration of the bottle crates is inspected or detected by the degree of fading of the coloring pigment or the appearance such as gloss of the surface, such a process is unreasonable because the inferiority of appearance is not directly related to strength. Further, such an inspection of appearance is not efficient, and such a process is liable to cause errors.

SUMMARY OF THE INVENTION

It is therefore an object of the present invention to provide an apparatus for rejecting or sorting out defective crates by which crates which cannot be used due to the strength decrease are accurately and automatically discriminated and sorted out from other sound bottle crates.

This and other objects of the present invention will be more readily apparent from the following description when read in connection with the accompanying drawings.

According to the present invention, there is provided an apparatus for discriminating and sorting out defective crates comprising driving means for urging an indenter or contact tip provided at a tip of a vibrating rod of an ultrasonic hardness tester into steady contact in indented state with a part of a crate, detecting means for detecting resonant frequency of the vibrating rod which is varied by the urging of the indenter or contact tip into steady contact with the crate, and means for distinguishing and sorting out defective crates from sound crates in response to the resonant frequency detected by the detecting means.

DETAILED DESCRIPTION OF THE INVENTION

Figure 1:
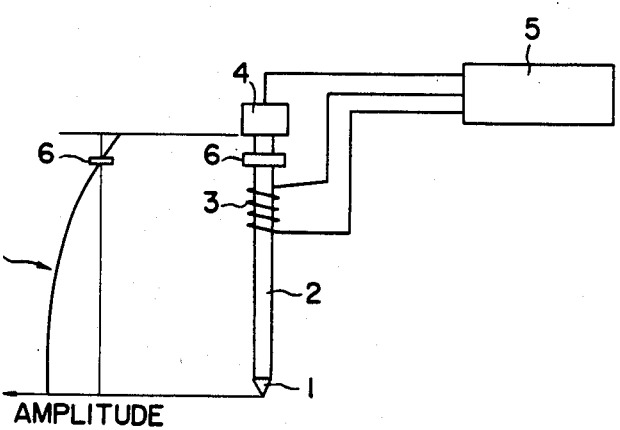
FIG. 1 is a combination of a schematic diagram and a graphical representation indicating the principle of an ultrasonic hardness tester which is used in the present invention.

FIG. 1 is a combination of a schematic diagram and a graphical representation indicating the principle of a known ultrasonic hardness tester used in the present invention. A metal vibrating rod 2 made of Ni alloy, for example, has at its distal end an indenter or contact tip 1 in the form of for example a Vickers diamond penetrator. An exciting or energizing coil 3 is wound around the vibrating rod 2. A piezoelectric pick-up member 4 made of barium titanate for example, is attached to the base or proximal end of the vibrating rod 2. The exciting coil 3 and the piezoelectric pick-up member 4 are electrically connected to an oscillator 5. The vibrating rod 2 is fixed to a fixing member 6 at an intermediate position between the exciting coil 3 and the piezoelectric pick-up member 4.

Figure 2:
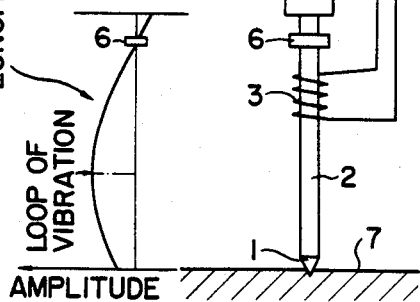
FIG. 2 is an illustration similar to FIG. 1 indicating the change of vibration state when an indenter provided at a tip of a vibrating rod of the hardness tester shown in FIG. 1 is urged into steady contact with plastic material.

When the vibrating rod 2 is subjected to longitudinal vibration, the vibrating rod 2 is vibrated at a resonant frequency at which the distal end having the indenter 1 forms a loop or antinode of vibration (point of maximum value of amplitude). When the indenter 1 provided at the tip of the vibrating rod 2 subjected to resonance is urged into steady contact with the surface of plastic material 7 under a constant load as shown in FIG. 2, the indenter 1 is subjected to a restraining force which is determined by hardness of the surface of the plastic material 7 and its Young's modulus. Thus the loop of vibration moves from the tip of the vibrating rod 2 to an intermediate position, whereby the resonant frequency varies.

The material of the indenter 1 is not restricted provided that the Young's modulus thereof is at least 10 times greater than that of the plastic material 7 of the crates. In addition to diamond, metals such as stainless steels and ceramics such as TiC, SiC and WC can be used.

It is desirable that the shape of the tip of the indenter 1 be conical and that the vertex angle thereof of be within the range of from 130° to 160°.

The following tests were carried out on polyethylene crates for beer bottles on the basis of the principle as briefly described above. The Vickers diamond indenter 1 provided at the tip of the vibrating rod 2 was urged into steady contact with the side walls of each crate to measure the resonant frequencies. Thereafter, a drop impact test of the crate was carried out as a practical strength test to determine the drop height at which breakage takes place.

The indenting or contacting load of the Vickers diamond indenter 1 was set at 1 kg. The reason why the Vickers diamond indenter 1 was urged into steady contact with the side walls of the crate is that because the side walls of the crate, in general, are thinner than other parts and have the least strength, the measurement of the deteriorated state of these side walls is reasonable.

The drop test was carried out by dropping the crate which was packed with iron bottles corresponding to the weight of the content-containing bottles from specific heights at a test temperature of 10±1° C. so that a corner of the crate collided with a concrete floor surface. The drop height was increased in order from 0.7 meters, through 1, 2, 3 and 4 meters. The lowermost height at which breakage of the crate took place was taken as the breaking height.

Figure 3A:
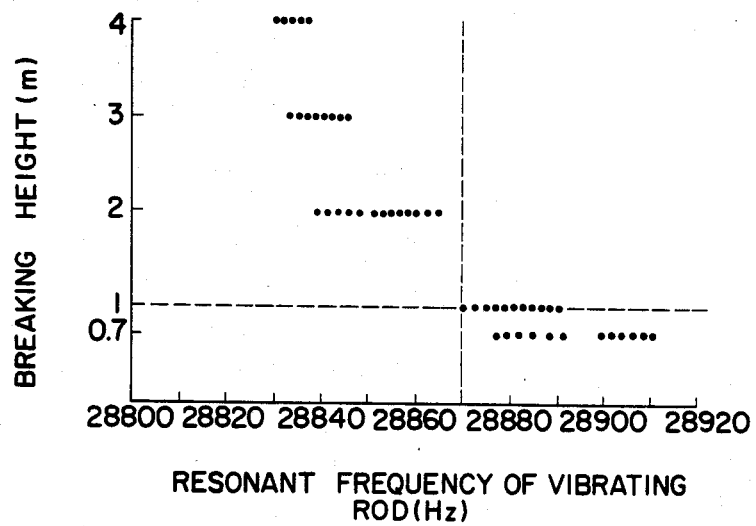
FIG. 3A is a graph indicating the relationship between breaking height in a drop test of crates and the vibratory frequency of a vibrating rod in a resonant frequency test.

The results of these tests are shown in FIG. 3A. As can be seen from this figure, the crates showing resonant frequencies above 28,870 Hz were all broken at a drop height of from 0.7 to 1 meter. Thus, a considerable decrease in strength was observed. It is believed that the reason why the crates having lowered strength have high resonant frequency is as follows. When the strength is lowered (i.e., the molecular weight of the polymer of the surface is decreased as stated hereinbefore to form fine cracks, and the crates become brittle), the force for restraining the diamond indenter 1 provided at a tip of the vibrating rod 2 is increased. On the other hand, it is believed that the reason why the crates still having high strength have low resonant frequency is that, because such crates are subject to elastic deformation, the restraining force with respect to the diamond indenter 1 is lower than that of the crates having lowered strength.

Thus, if the indenter 1 is urged into steady contact with a crate to measure the resonant frequency of the vibrating rod 2, then the deterioration state of the bottle crate can be detected.

In the experimental example as described above, the indenting or contacting load of the indenter 1 was 1 kg and the discriminating threshold distinguishing sound crates from defective crates was a breaking drop height of 1 meter. However, it is possible to control the discriminating threshold of the crates to be sorted out by varying the indenting or contacting load of the indenter 1.

Figure 3B:
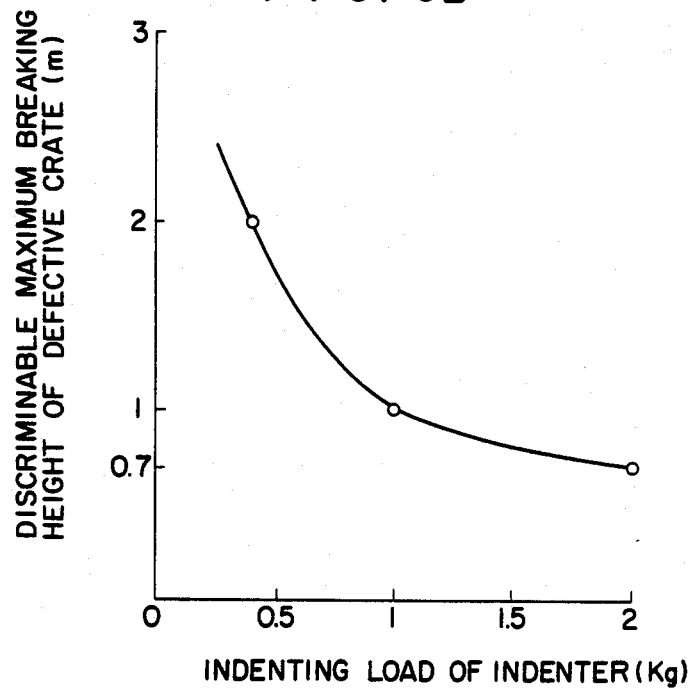
FIG. 3B is an example of a graph indicating the relationship between the indenting load of an indenter and discriminating threshold of the breaking drop height or the discriminable maximum breaking drop height of crates.

FIG. 3B indicates the results obtained from an examination of the relationship between the discriminable maximum breaking drop height of crates (polyethylene bottle crates for beer bottles) and the contacting load of Vickers diamond indenter. As can be seen from FIG. 3B, when the discriminating threshold distinguishing the sound crates and the defective crates is set at breaking drop heights of 2 meters, the contacting load of the indenter may be about 0.5 kg.

Figure 4:
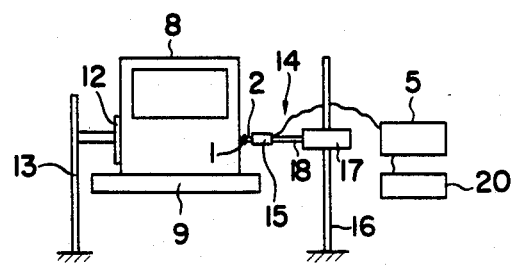
FIG. 4 is a view in the downstream direction of a production line of an example of the apparatus for sorting out defective crates according to the present invention which is installed in the line.
Figure 5:
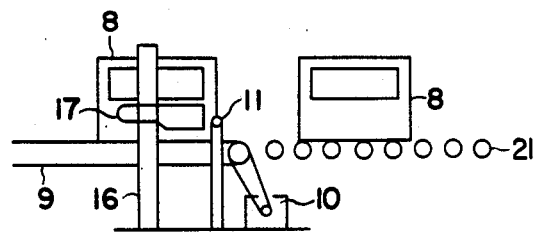
FIG. 5 is a side elevation of the apparatus shown in FIG. 4.
Figure 6:
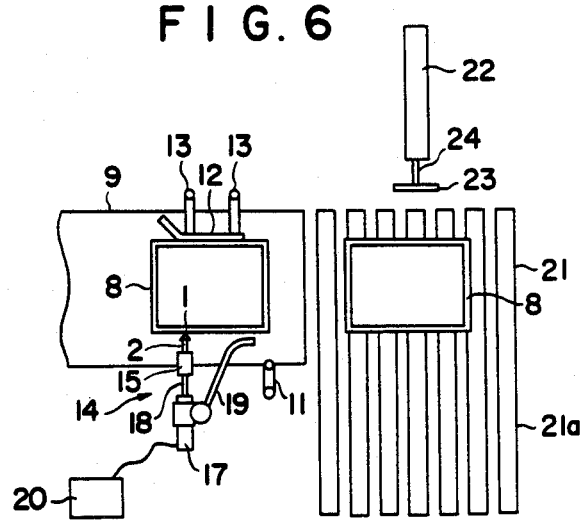
FIG. 6 is a plan view of the apparatus shown in FIG. 4.

FIG. 4–FIG. 6 illustrate an example of an apparatus for detecting and rejecting defective plastic bottle crates according to the present invention, which operates in conjunction with a belt conveyer 9 for horizontally conveying crates 8. When a crate 8 reaches a predetermined inspection position or station, on the belt conveyer 9, the crate is detected by a photoelectric switch 11. An electromagnetic clutch coupled to a driving motor 10 of the belt conveyer 9 is disengaged by the resulting signal of the switch 11, whereby the belt conveyer 9 is stopped, and thus the detected crate 8 is stopped at the inspection station.

A back-up guide plate 12 for preventing sidewise movement in the transverse direction of the crate 8 which has stopped at the inspection station is supported by a support stand 13 so that the guide plate 12 extends above the conveyer 9 in the advance direction of the crate 8 and functions as a back-up structure for the crate 8 on the belt conveyer 9.

An ultrasonic hardness tester 14 as illustrated in FIG. 1 is disposed on the other side of the belt conveyer 9 opposite the stand 13. The vibrating rod 2 of this ultrasonic hardness tester 14 is so supported at its base portion by a supporter 15 as to direct the indenter or contact tip 1 toward the crate 8. The supporter 15 is provided at the tip of a piston rod 18 of an air cylinder 17 which is mounted on a stand 16, and therefore the vibrating rod 2 can be advanced to or retracted from a side wall of the crate 8 by supplying air into the air cylinder 17. The stand 16 is provided with a guide plate 19 made of an elastic material. The guide plate 19 has a curved distal end portion and projects toward the crate 8. This guide plate 19 and the guide plate 12 are so disposed and adapted that they can grip the crate 8 therebetween.

The contacting force of the indenter 1 against the crate 8 is maintained constant by energizing the vibrating rod 2 with a spring (not shown) in the supporter 15. When the plastic material from which the crate 8 is produced is polyethylene or polypropylene, the contacting force is suitably from about 0.5 kg to 2 kg. The fundamental vibration frequency of the vibrating rod 2 is suitably from about 20 KHz to about 30 KHz.

A resonant frequency meter 20 is connected to an oscillator 5 of the vibrating rod 2. Resonant frequencies applied by urging the indenter 1 into steady contact with the crate 8 are measured with a precision of ±1 Hz by means of the resonant frequency meter 20. When a resonant frequency is above a set value, a built-in discriminating circuit (not shown) produces an output signal indicating that the crate 8 being inspected is defective.

A roller conveyer 21 is disposed at the downstream side of the above described inspection station. The roller conveyer 21 is made to have a wide width so that two crates can be placed thereon in parallel. The roller conveyer 21 includes an auxiliary mounting portion 21a. An air cylinder 22 to sort defective crates from sound crates 8 is disposed at one side of the roller conveyer 21. A piston rod 24 of the air cylinder 22 which has a pressing plate 23 at one end projects transversely over the roller conveyer 21 to push defective crates toward the auxiliary mounting portion 21a. For this purpose, the air cylinder 22 is driven upon receiving a signal from the discriminating circuit of the resonant frequency meter 20.

The operation of the above described example according to this invention is as follows.

When each of the crates 8 to be checked and being conveyed in a row on the belt conveyer 9 reaches the inspection station, the electromagnetic clutch (not shown) coupled to the driving motor 10 of the belt conveyer 9 is disengaged in response to the detection signal from the photoelectric switch 11, whereby the belt conveyer 9 is stopped, and the crate 8 is stopped at the inspection station. In this state, the crate 8 is gripped by the pair of guide plates 12 and 19 and thereby steadily held.

Air is then supplied to the air cylinder 17 to extend the piston rod 18, and thus the indenter 1 provided at the tip of the vibrating rod 2 is urged into steady contact with a side wall of the crate 8 with constant force by the action of the spring (not shown) in the supporter 15. At this time, resonant frequency of the vibrating rod 2 is measured by means of the resonant frequency meter 20. If a frequency thus determined exceeds a specific value), that is, if it is indicated that marked deterioration of the plastic crate has taken place, a signal indicating that the crate 8 is defective will be transmitted from the discriminating circuit to the air cylinder 22.

Thereafter, the electromagnetic clutch coupled to the driving motor 10 is engaged to drive again the belt conveyer 9, and the vibrating rod is retracted. Thereupon the crate 8 whose resonant frequency has been measured is conveyed toward the downstream side of the inspection station, and the succeeding crate 8 reaches the inspection station and is detected by the photoelectric switch 11. Thus, the belt conveyer 9 is again stopped and measurement of resonant frequency is carried out according to the procedure described above.

On the other hand, the crate 8 conveyed onto the roller conveyer 21, disposed on the downstream side of the inspection station, is handled as follows. when the resonant frequency of the crate 8 is above the set value, a signal is transmitted from the discriminating circuit of the resonant frequency meter 20 to the air cylinder 22, whereby the piston rod 24 of the air cylinder 22 extends to move the defective crate 8 to the auxiliary mounting portion 21a. The defective crate is conveyed from the above described position to a stacking place (not shown) by means of other conveyers (also not shown).

When the resonant frequency of the crate 8 is less than the set value, a signal is not transmitted to the air cylinder 22, and therefore the piston rod 24 of the air cylinder 22 remains in its retracted state. Thus, the crate 8 is conveyed on the roller conveyor 21 until it reaches a specific position. In the meanwhile, when the piston rod 24 of the air cylinder 22 is once extended, it is retracted immediately.

Because the time required to transmit the signal indicating that the crate 8 is defective from the resonant frequency meter 20 to the air cylinder 22 is within about 2 seconds after the crate 8 has reached the inspection station, the discrimination of the defective crate can be carried out very rapidly and accurately.

As described above, the apparatus for discriminating defective plastic bottle crates according to the present invention comprises a driving device for urging the indenter or contact tip provided at the tip of the vibrating rod of the ultrasonic hardness tester into steady contact with the crate, a detecting device for detecting the resonant frequency of the vibrating rod which is varied by the urging of the indenter or contact tip into steady contact with the crate, and a device for distinguishing defective crates from sound crates in response to the resonant frequency detected by the detecting device. Accordingly, discrimination between crates having significantly lowered strength and sound crates can be automatically, rapidly and accurately carried out as the crates are conveyed in succession.

What is claimed is:

1. A method of sorting out defective plastic crates for bottles, each said defective crate being made of one piece molded plastic having substantially lost its inheritent mechanical properties, said method being based on a chemical differentiating between a new and a worn plastic material, said method comprising of the following steps:
   (a) conveying of a plurality of the crates to an inspection station;
   (b) bringing an individual crate into the inspection station and keeping said crate at the inspection station in an equilibrium state;
   (c) applying a vibrating rod with an indenter at its distal tip of an ultrasonic hardness tester to an entire outside surface of the crate and keeping the vibrating rod and the indenter in a steady contact with the crate;
   (d) detecting a resonant frequency by the vibrating rod, said resonant frequency is varied by the indenter within the crate;
   (e) discriminating the detected resonant frequency of the crate depending on whether the resonant frequency of the crate exceeds a predetermined level, the resonant frequency exceeding the predetermined level is caused by a layer formed on the outside surface of the crate due to a long use thereof, said distal tip of the indenter penetrating into the layer;
   (f) conveying the crate out of the inspecting station; and
   (g) sorting out defective plastic crates from the plurality of the tested crates depending on detected response of each said crate to the discriminating of the resonant frequency in a such manner that a plastic crate having a resonant frequency exceeding the predetermined level is classified as the defective plastic crate.

2. A method according to claim 1 wherein said vibrating rod has a longitudinal axis and is subjected to vibrations along said longitudinal axis.

3. A method of sorting out defective plastic crates which have been worn with a long use as claimed in claim 1 wherein the predetermined level of the resonant frequency is 28870 Hz.

4. A method according to claim 1 wherein the resonant frequency of vibrating rod is in the range from 20 KHz to 30 KHz.

5. A method according to claim 1 wherein the distal tip of said indenter is conical and has a vertex angle within the range of from 130° to 160°.

* * * * *